United States Patent
Dunn et al.

(10) Patent No.: US 10,054,531 B2
(45) Date of Patent: Aug. 21, 2018

(54) APPARATUS AND METHOD FOR MONITORING A SEDIMENTATION PARAMETER IN A FLUID MEDIUM SAMPLE

(71) Applicant: MICROVISK LIMITED, St. Asaph Denbigshire (GB)

(72) Inventors: Richard John Dunn, St. Asaph (GB); Lois Bello Fernandez De Sanmamed, St. Asaph (GB); Robert Henry Ibbotson, St. Asaph (GB); Vladislav Djakov, St. Asaph (GB)

(73) Assignee: Microvisk Limited, St Asaph (GB)

( * ) Notice: Subject to any disclaimer, the term of this patent is extended or adjusted under 35 U.S.C. 154(b) by 460 days.

(21) Appl. No.: 14/646,562

(22) PCT Filed: Mar. 12, 2013

(86) PCT No.: PCT/GB2013/050607
§ 371 (c)(1),
(2) Date: May 21, 2015

(87) PCT Pub. No.: WO2014/083300
PCT Pub. Date: Jun. 5, 2014

(65) Prior Publication Data
US 2015/0316461 A1    Nov. 5, 2015

(30) Foreign Application Priority Data
Nov. 28, 2012   (GB) .................................. 1221432.6

(51) Int. Cl.
*G01N 15/05*   (2006.01)
*G01N 29/02*   (2006.01)
(Continued)

(52) U.S. Cl.
CPC ............. *G01N 15/05* (2013.01); *G01N 15/04* (2013.01); *G01N 15/06* (2013.01);
(Continued)

(58) Field of Classification Search
CPC ... G01N 15/05; G01N 2015/055; G01N 15/04
(Continued)

(56) References Cited

U.S. PATENT DOCUMENTS 5,914,272 A * 6/1999 Dufresne ............... G01N 15/05
                                            422/550
6,096,559 A    8/2000  Thundat et al.
(Continued)

FOREIGN PATENT DOCUMENTS

GB       2491806 A       12/2012
WO    WO 2004/029625 A2   4/2004
(Continued)

OTHER PUBLICATIONS

PCT Notification of Transmittal of the International Search Report and the Written Opinion of the International Searching Authority, or the Declaration; PCT International Search Report; PCT Written Opinion of the International Searching Authority for PCT/GB2013/050607, dated Aug. 2, 2013, 13 pgs.
(Continued)

*Primary Examiner* — Erik B Crawford
(74) *Attorney, Agent, or Firm* — Patterson Thuente Pedersen, P.A.

(57) ABSTRACT

There is provided a method of measuring a sedimentation parameter of suspensions or precipitants in a fluid medium sample, said method compromising providing at least one micro-cantilever sensor, said micro-cantilever sensor comprising at least two materials having different coefficients of thermal expansion, and having a heater and piezo-resistive sensor integrated therein, pulsing the heater with one or
(Continued)

more electrical pulses to induce heat generation in the micro-cantilever, sampling the output of the integrated piezo-resistive sensor to characterize a response of the micro-cantilever during sedimentation in the fluid medium sample, and determining a value of the sedimentation parameter from the characterized response. There is also provided an apparatus arranged to carry out the method.

15 Claims, 8 Drawing Sheets

(51) Int. Cl.
*G01N 15/06* (2006.01)
*G01N 15/04* (2006.01)
*G01N 33/49* (2006.01)
*G01N 29/036* (2006.01)

(52) U.S. Cl.
CPC ....... *G01N 15/0606* (2013.01); *G01N 29/022* (2013.01); *G01N 33/491* (2013.01); *G01N 29/036* (2013.01); *G01N 2015/055* (2013.01)

(58) Field of Classification Search
USPC .......................................... 436/70; 73/61.65
See application file for complete search history.

(56) References Cited

U.S. PATENT DOCUMENTS

| | | | | |
|---|---|---|---|---|
| 6,575,020 | B1* | 6/2003 | de Charmoy Grey | G01N 9/002 73/53.01 |
| 2002/0092340 | A1* | 7/2002 | Prater | G02B 7/1821 73/24.02 |
| 2002/0139190 | A1 | 10/2002 | Daraktchiev et al. | |
| 2005/0244820 | A1* | 11/2005 | Su | C12Q 1/6825 435/5 |
| 2008/0068000 | A1 | 3/2008 | Bargatin et al. | |
| 2009/0139340 | A1 | 6/2009 | King et al. | |
| 2009/0165559 | A1* | 7/2009 | Lec | G01N 33/53 73/579 |
| 2010/0251806 | A1 | 10/2010 | Djakov | |
| 2011/0053285 | A1* | 3/2011 | Jeon | G01N 21/4738 436/164 |
| 2011/0129929 | A1* | 6/2011 | Day | G01N 9/002 436/8 |
| 2012/0043203 | A1* | 2/2012 | Lin | G01N 1/16 204/403.06 |
| 2012/0090387 | A1 | 4/2012 | Djakov | |
| 2013/0118228 | A1* | 5/2013 | Parpia | G01N 29/022 73/23.3 |
| 2013/0266930 | A1* | 10/2013 | Dinges | G01N 33/5375 435/5 |

FOREIGN PATENT DOCUMENTS

| | | |
|---|---|---|
| WO | WO 2005/054817 A1 | 6/2005 |
| WO | WO 2007/011364 A1 | 1/2007 |
| WO | WO 2007/104978 A1 | 9/2007 |

OTHER PUBLICATIONS

GB Combined Search and Examination Report for GB1221432.6, dated Mar. 6, 2013, 8 pgs.
GB Amended Examination Report for GB1221432.6, dated Apr. 9, 2014, 2 pgs.
Hutchinson, R.M., et al., "A comparison of the erythrocyte sedimentation rate and plasma viscosity in detecting changes in plasma proteins", *From the Department of Haematology, Frenchay Hospital, Bristol, J. clin. Path.*, 1977, 30, pp. 345-349.

* cited by examiner

APPARATUS AND METHOD FOR MONITORING A SEDIMENTATION PARAMETER IN A FLUID MEDIUM SAMPLE

RELATED APPLICATIONS

The present application is a National Stage entry of International Application No. PCT/GB2013/050607 filed Mar. 12, 2013, which claims the benefit of GB Application No. 1221432.6, Nov. 28, 2012, said applications being hereby incorporated by reference in their entirety.

FIELD OF THE INVENTION

This invention relates to methods and measurement devices for measuring the sedimentation or diffusion of suspensions or precipitants in a fluid medium sample in general, and in particular to determining sedimentation or diffusion rate, using a self-sensing micro-cantilever fluid probe sensor.

BACKGROUND OF THE INVENTION

Measurement of the sedimentation (or ability of suspended particles to settle within a liquid, under the influence of gravity), buoyancy (or ability of suspended particles to rise in the fluid) of suspensions or precipitants or diffusion rates in a fluid medium may be useful in a variety of areas, such as medical diagnostics, mechanical/industrial processing (or processing machinery testing), environmental monitoring or the like. Such measurements may be the result of sample separation due to difference of density or a reaction between fluid suspensions and a reagent. Sedimenting particle mass, shape and size all impact sedimentation rate and these properties may be estimated from measured sedimentation rates. For example, in medical diagnostics, Erythrocyte Sedimentation Rate (ESR) is one of the most frequently performed medical laboratory tests, reflecting the rate at which red blood cells separate from the plasma due to gravity in a static vertical vessel. The sedimentation rate (measured in mm/hour) is determined macro-morphologically by measuring the distance from the top cellular level to the top of plasmatic level after 60 minutes or so of uninterrupted settling time.

There are known methods to measure the sedimentation rate of suspensions in a fluid but they each have associated disadvantages, including time to answer, sample preparation, size of equipment, cost or complexity to carry out, and the like. For example, optical techniques (such as laser sources) can only be used in a transparent bulk fluid medium.

SUMMARY OF THE INVENTION

There is provided a method of measuring a sedimentation parameter of suspensions or precipitants in a fluid medium sample, said method compromising providing at least one micro-cantilever sensor, said micro-cantilever sensor comprising at least two materials having different coefficients of thermal expansion, and having a heater and piezo-resistive sensor integrated therein, pulsing the heater with one or more electrical pulses to induce heat generation in the micro-cantilever, sampling the output of the integrated piezo-resistive sensor to characterise a response of the micro-cantilever during sedimentation in the fluid medium sample, and determining a value of the sedimentation parameter from the characterised response.

In this description, the term measuring includes monitoring.

The method may further comprise determining a property of a predetermined reaction in the fluid medium sample from the determined value of sedimentation parameter, wherein the property comprises the existence or extent of a predetermined (i.e. specified) reaction.

The method may further comprise determining a percentage volume of suspension.

The method may further comprise calibrating the at least one micro-cantilever response to a percentage volume of suspension in known standards to form a calibrated micro-cantilever response characteristic, optionally wherein the known standard is a haematocrit standard.

The fluid medium sample may comprises a biological sample, and the reaction may then include any one or more of: erythrocyte sedimentation rate; and precipitation immunoassay.

The sedimentation parameter of suspensions or precipitants may comprise any one of: a rate of sedimentation; an existence or not of sedimentation; a predetermined amount of sedimentation; a nominal absolute value of sedimentation; a suspension concentration; and a haematocrit value.

The sedimentation parameter of suspensions or precipitants may be due to the product of, or directly due to, one or more reactions.

The sedimentation parameter of suspensions or precipitants or flock may be due to the product of, or directly due to, the action of a flocking agent.

The method may further comprise measuring, based upon the measured sedimentation parameter, any one or more of: diffusion or perfusion rate across membranes within the fluid medium, diffusion of suspensions or precipitants detached from a surface within the fluid medium, or cellular adhesion within the fluid medium.

The method may further comprise a simultaneous measurement of temperature of the fluid medium using the micro-cantilever and correcting the measured sedimentation value based on the temperature, wherein the temperature may be measured using the piezo-resistive sensor, or an alternately configured heater (for example in 'read-out of temperature' mode).

The at least one (or more) micro-cantilever sensors may be physically distributed around (or throughout, on an inner surface of) a sample test chamber containing the fluid medium, or within an entity that makes use of a fluid medium under test, to gain location specific monitoring of sedimentation values within the fluid medium under test.

The at least one micro-cantilever sensor comprises a plurality of micro-cantilevers, wherein the plurality of micro-cantilevers may be physically distributed along an axis along which the sedimentation acts. The axis along which the sedimentation acts may be defined as an axis parallel to the action of gravity or centrifugal force.

The method may further comprise providing at least two substantially similar micro-cantilevers, wherein a first micro-cantilever is placed in a first fluid medium and a second micro-cantilever is placed in a second fluid medium, wherein the method further comprises comparing the output of a piezo-resistive sensor integrated into the first micro-cantilever with the output of a piezo-resistive sensor integrated into the second micro-cantilever when both are immersed in the respective first and second fluid mediums.

The first fluid may be a control fluid, the second fluid medium may comprise suspensions. The first micro-cantilever may be a control micro-cantilever and the second micro-cantilever may be a (sedimentation) measurement micro-cantilever.

The first fluid may be a first sample of the fluid medium comprising suspensions, the second fluid may be a second sample of the fluid medium comprising suspensions, the first micro-cantilever may be a measurement micro-cantilever in a first position and/or orientation and the second micro-cantilever may be a measurement micro-cantilever in a second position and/or orientation.

The method may further comprise inverting the at least one micro-cantilevers in use (e.g. by inverting the overall device, or by activating an internal means to invert the relevant micro-cantilevers), and/or re-pulsing the heater with one or more electrical pulses to induce heat generation in the micro-cantilever, and/or re-sampling the output of the integrated piezo-resistive sensor to characterise an inverted response of the micro-cantilever during sedimentation in the fluid medium sample, and/or determining a value of the sedimentation parameter from the characterised inverted response.

There is also provided an apparatus adapted or arranged to carry out any of the described methods.

There is also provided an apparatus for measuring a sedimentation parameter of suspensions or precipitants in a fluid medium sample, compromising at least one micro-cantilever sensor, said micro-cantilever sensor comprising at least two materials having different coefficients of thermal expansion, and having a heater and piezo-resistive sensor integrated therein, heat generation means arranged to pulse the heater with one or more electrical pulses to induce heat generation in the micro-cantilever, sampling means arranged to sample the output of the integrated piezo-resistive sensor to characterise a response of the micro-cantilever during sedimentation in the fluid medium sample, and logic arranged to determine a value of the sedimentation parameter from the characterised response.

The apparatus may further comprise a sample test chamber having two sub-chambers (or two test chambers, with or without fluid communication between—depending on how the two chambers are filled with the fluid sample, and whether they are to be mixed or not during testing/measurement), wherein the at least one micro-cantilever comprises two micro-cantilevers, wherein one micro-cantilever is located in each of the two sub-chambers. In such dual chamber/dual micro-cantilever embodiments, the two micro-cantilevers may be located diametrically opposite one another during use, such that one may operate to test for sedimentation (i.e. concentration of particles under the influence of gravity or centrifugal force in downward direction), and the other for buoyancy (i.e. concentration of particles under the influence of upwards force, exerted by liquid). In another embodiment a plurality of micro-cantilevers may be distributed in such a way so that diffusion of particles, radially from the source of higher concentration (not highly directional as sedimentation or buoyancy) can be monitored.

The apparatus may comprise two further micro-cantilevers, wherein each of the two sub-chambers of the sample test chamber has two micro-cantilevers, each micro-cantilever located opposite one another at either end of the test chamber, along an axis of interest.

The axis of interest may be the axis along which gravity or another force acts.

Embodiments also provide testing apparatus comprising at least one micro-cantilever. These micro-cantilevers may be arranged to carry out any herein described method. The at least one micro-cantilever may be (pre-use) calibrated at manufacture, with a digital memory operable coupled to the micro-cantilever, and/or a reading device and/or a removal cartridge containing the at least one micro-cantilever, for use with the reading device, such that the (pre-use) calibration is available for correction with outputs of the micro-cantilever during use in any described methods.

Where measurement of a parameter of sedimentation (e.g. rate of deposition or formation of sediment) is discussed herein, buoyancy (i.e. propelling of particles in opposite direction to the one of sedimentation) measurement may also be meant. These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

Figure 1:
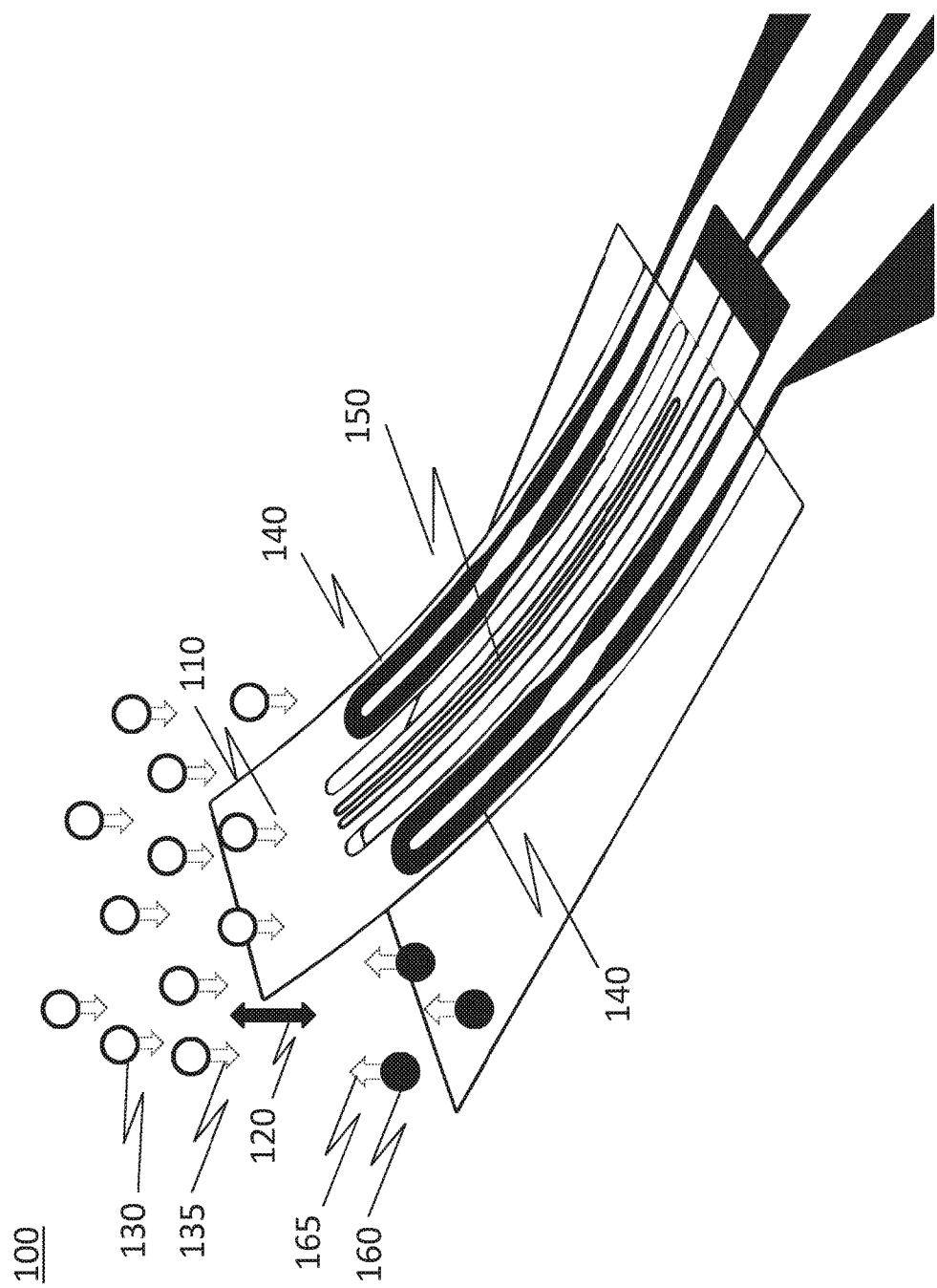
FIG. 1 shows a side perspective view of a micro-cantilever based sensor for measuring sedimentation according to an example embodiment of the present invention.

Embodiments and examples of the present invention provide a measurement device and method for the measurement of sedimentation rate of suspensions or precipitants within a fluid medium (sample, or in-situ testing of fluids) (such as Erythrocyte Sedimentation Rate, or the like), using a self-sensing micro-actuator, as described in more detail below. The described micro-actuator based sensor probe is disclosed in the form of a micro-cantilever, or beam, but other physical forms of sensor may be realised.

The term 'fluid medium sample' used herein may refer to either a singular fluid or a combination of two or more fluids, or a mixture of one or more fluids with another medium causing a reaction, e.g. catalyst, flocking agent or the like. The term 'fluid medium sample' may also include physical or complex suspensions in the one or more fluid(s) medium(s), for example particulate suspensions comprising both (semi-) solid portions as well as the fluid(s), such as liquids or gas. The particulates may be the interactive portion of the fluid medium sample, for example when they are formed as a coagulate, floc or the like. In a broad sense, the fluid medium sample may be any chemical sample, or biologic sample taken from a specimen, suitable for testing.

The measurement device may form part of a dynamic micro test/diagnostic system that is sensitive to the measurement of sedimentation rate or diffusion rate (where 'diffusion' is used herein to mean the opposite of sedimentation, i.e. where the particles rise relative to the bulk fluid medium) of suspensions or precipitants of one or more specified reactions in a fluid medium sample, over time, and may also provide a unique parallel function as an initial mixer (i.e. starting/aiding the interaction(s) in the fluid medium sample under test that lead to the sedimentation/diffusion of suspensions), and therefore may also help to accelerate the start of any chemically driven sedimentation. The micro-cantilevers may be coated, at least in part, for example with a catalyst for the reaction creating the sedimentation or buoyant particles, and as such the choice and amount of any added micro-cantilever coating may be use dependent). Such a system is particularly applicable to measurements involving biological and chemical suspensions in a fluid. The disclosed method and device also has lower power requirements compared to standard known fluid sedimentation testing methods.

The measurement device may be used to simultaneously measure the sedimentation rate of suspensions or precipitants within a fluid medium sample and the suspension volume percentage in the fluid medium sample to allow compensation, and therefore higher accuracy, of the sedimentation rate measurement.

The disclosed method and device also has high sensitivity and may provide a (relatively) immediate response in low volume compared to standard known methods for sedimentation rate measurement, and may provide a rate correction based on calibration in known fluid medium examples, e.g. having a known volume percentage of suspension fluid medium, or particles, etc.

A plurality of such micro-actuator based sensors may be utilised together, for example in an array, grid or other distribution around/across/throughout a fluid medium test chamber to form a differential sensor apparatus/system or area/volume testing system as described in more detail below. The present description includes the results of experiments carried out on embodiments of the invention to assess the ability of the micro-actuator based method and measurement device(s) according to the invention to measure sedimentation of suspensions or precipitants in a fluid medium sample.

FIG. 1 shows a side perspective view of the dynamic self-sensing micro-cantilever based micro-actuator measurement device 100 according to an example embodiment of the present invention. In particular, this figure illustrates how the micro-cantilever actuator 110 may mechanically sweep 120 the bulk fluid medium, having particle suspensions or precipitants 130 therein, under control of at least one integrated micro-heater 140 with the movement of the micro-cantilever as a whole being sensed using at least one movement sensor 150. The micro-heater 140 and sensor 150 may be embedded in the micro-cantilever, and the micro-cantilever may extend out-of plane into the fluid medium sample. Suspensions 130 with higher density to the bulk fluid medium will move down (i.e. under gravity) 135 and sediment to the bottom of the chamber at a constant rate, measured as the sedimentation rate. Similarly, suspensions with lower density to the bulk fluid medium 160 (and that can/will be detached from a surface) will have a diffusion rate upwards (i.e. in opposite direction to the action of gravity) 165 in the fluid medium, and both these types of "sedimentation" rates can be measured by the described micro-cantilever sedimentation sensors, to thereby characterise or simply confirm a reaction and/or indicate the strength and rate of sedimentation/buoyancy, or related parameters. The measurement device may also measure a biological or chemical reaction that leads to suspensions dropping out of solution and sedimenting.

One disadvantage of a typical micro-cantilever arrangement is that the micro-cantilever is formed of a relatively rigid material, such as silicon, thus limiting the deflection range (and therefore sensitivity) of the sensor with respect to probing micro-rheological properties of a fluid/liquid sample. Limited deflection requires high resolution readout of the micro-cantilever deflection using optical lever or interferometer techniques which are bulky, require alignment and calibration, and are therefore unsuitable for simple, portable devices. A disadvantage of a typical passive system (relying on binding on the surface) is a proportionally large background and system noise (due to unspecific binding and mechanical changes through absorption). Such systems also have very low (<1 micron) deflection requiring high resolution read-out methods.

The micro-cantilever based sensor according to example embodiments of the invention may be formed as a beam attached to a body by a first end, with a second end distance from the first end that is free to move in relation to the body. The micro-cantilever beam typically has a rectangular surface area, with the longer side of the rectangle extending from the body. The micro-cantilever may comprise a laminate of at least two layers of material, the materials of each layer having different coefficients of thermal expansion (i.e. providing a bi-morph structure). The materials can be different materials, or the same material processed (e.g. stressed) so as to have different coefficients of thermal expansion. One exemplary material suitable for forming the laminate of at least two layers is polyimide.

Under application of heat, one layer will expand more than the other for the same rise in temperature, and hence the micro-cantilever will bend in the direction of the material with the lower coefficient of thermal expansion. Upon cooling, one layer will contract faster than another for the same decrease in temperature, and hence the micro-cantilever will then bend in the direction of the material with the greater coefficient of thermal expansion.

An actuating heater may be located on or in the micro-cantilever, and may comprise conductive material forming a continuous line or track across an area of the surface of the micro-cantilever. The heater may further comprise electrical contacts for delivery of current to (and resulting in heat dissipation from) the heater. These electrical contacts may be located on an upper surface of the body, in use, for ease of access.

One or more integrated movement sensor(s) may also be located on or in the micro-cantilever, and may also comprise conductive material forming a continuous line or track across an area of the surface of the micro-cantilever. The movement sensor may be formed from piezo-resistive material, which may also provide thermal sensing abilities, by sensing changes in resistance due to temperature changes.

Wheatstone bridge circuits may be used to measure the output of the integrated movement sensor(s), as they are a particularly sensitive apparatus for the comparative measurement of capacitance and resistance. A Wheatstone bridge circuit may be used with the micro-cantilever to determine the amount of movement (i.e. bending) of the micro-cantilever, or other properties (or change in properties) of the overall micro-cantilever sensor system, such as thermal properties. The Wheatstone bridge may be located on the body of the micro-cantilever, or remote from the micro-cantilever sensor, but coupled to electrical contacts of the respective parts of the micro-cantilever sensor, such as integrated sensors(s). In use, a voltage is applied across the Wheatstone bridge circuit, and a voltage output is measured across the centre of the bridge. When the output of the bridge is zero, the bridge is said to be balanced and the resistances/capacitances equal. When the resistance/capacitance of one of the legs changes, due to a change in the output of the integrated sensor(s), the previously balanced bridge is now unbalanced. This change produces a voltage change across the centre of the bridge, from which an output of the overall apparatus can be derived, indicative of a property (or change in property, or more than one property) of the fluid medium sample. When using resistive sensors, the resistance may change due to mechanical changes, thermal changes or both changes acting at the same time.

There may be provided multiple combined heater/sensors, with results taken from each and combined into an averaged overall result, or the like. The fluid medium may be sensed in micro-liter or even sub-micro-liter sized samples. The micro-actuator may sense fluid/coagulate properties using movement and/or thermal based physical property measurements of the fluid medium. The rate and magnitude of the response is dependent on the kinetics of the particular reaction, sedimentation, separation or the like rheological process in a sample under test, and can be used to quantify the reaction and/or rheological process. It may be important that the sweeping pulse is then balanced through the actuation voltage or pulse width to move in a domain where agitation is minimised and the measurement of sedimentation rate is dominant.

Figure 2:
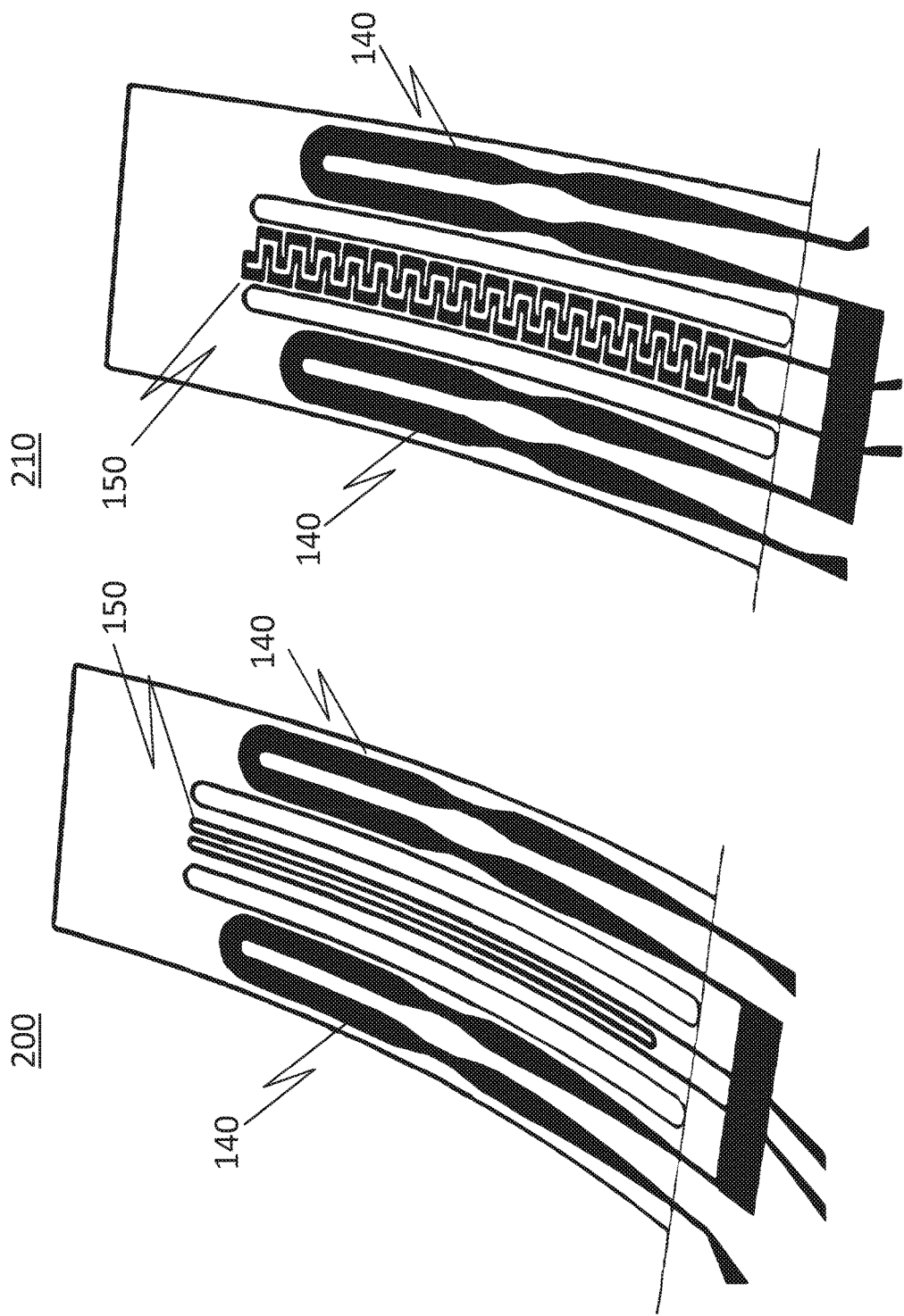
FIG. 2 shows top perspective views of two different example configurations of a micro-cantilever based sensor according to example embodiments of the present invention.

FIG. 2 shows two suitable alternative arrangements 200, 210 of integrated heater and movement sensor in the form of micro-cantilevers, both including a heater 140, and a movement sensor 150, but where the sensor 150 on the left hand version 200 is formed in a serpentine manner along the length of the micro-cantilever, and the sensor 150 on the right hand side 210 has a sensor 150 formed in a serpentine manner along the width of the sensor portion of the micro-cantilever. The different directions of the serpentine formation means the sensors are differently sensitive to longitudinal and linear strain, which may help isolate extraneous strain factors that might otherwise affect the results. For example, using the serpentine sensor on a second micro-cantilever allows that reference beam to be used actively, i.e. it can also be actuated. In the case where both sensors are the same, the actuation of both would cancel out the signal, because one cantilever is located on the positive arm of the Wheatstone bridge and the other is located on the negative arm. When using a serpentine form of sensor on one of the micro-cantilevers, because the serpentine sensor only measures the potential thermal drift in resistance as opposed to bending, the actuation of both the active and reference micro-cantilevers gives a better purely mechanical signal.

For example, in the positive arm (of the Wheatstone bridge) the signal is derived from both the sensed mechanical and thermal properties, whilst in the reference negative arm (of the Wheatstone bridge) it is only thermal properties that are sensed. Thus, using a serpentine sensor configuration may provide the advantages of better isolation of mechanical and thermal signals. Moreover, because the thermal portion of the sensor output signals should cancel out when using differently configured sensors, such as the serpentine configurations, the test may be carried out at any pulse length such that larger sweeping may be used to agitate a reaction for faster kinetics, before returning to normal operation to measure sedimentation rate of precipitants or aggregations.

Various physical properties of particles determine their rate of sedimentation in a given fluid medium. For example, such physical properties include, but are not limited to: mass, shape, size, density and the like. Sedimentation rate measurements on fluid systems in which one or more properties of the fluid medium or particles can be fixed, or held within a constant range, can lead to quantitative and qualitative information on the particulate properties being extracted from their sedimentation rates.

Oil and other mechanical system lubricants, such as those used in engines and the like, keep contaminants in suspension when working effectively. Measurement of the sedimentation rate of these contaminants can provide useful information about parameters of the lubricant including the function and quality of the lubricant, function and quality/type of contaminants that are circulating in the lubricant and the function of the mechanical system as a whole. Therefore in-line measurement of sedimentation rates in these environments can provide advanced warning of mechanical deterioration, thereby allowing just-in-time maintenance (to efficiently reduce wear and tear and fatigue on mechanical parts, without excessive/over maintenance). This may provide, amongst other benefits, more efficient maintenance, as items need only be replaced when needed, rather than pre-emptively.

Similarly, in industrial processing fluid environments, such as wastewater treatment, foodstuff manufacture, and the like, measurements of sedimentation rates may be used to assess the efficiency of coagulants and flocculants added to sedimentation tanks, and the like, as part of the respective processing of the fluid. Food manufacturing also makes use of flocculants/coagulants, and so monitoring of sedimentation rates of these food manufacturing materials can provide information on the food stuffs being manufactured, such as maturity and can be linked to quality and flavour, especially for example in the brewing industry.

Thus there are a variety of reasons to provide an improved method and apparatus for measuring (or determining characteristics of) fluid sedimentations.

Furthermore, sedimentation rate is often one of the most frequently performed laboratory tests in health diagnostics, where, typically, the rate at which red blood cells separate from the plasma due to gravity is measured. This is because, when whole blood is allowed to stand for a period of time, the red blood cells settle out from the plasma, and this can be very useful in diagnosing medical conditions. The rate at which the red cells sediment out (i.e. fall/drop down due to gravity in this specific case, as the cells are more dense that the surrounding fluid, i.e. blood plasma) is known as the Erythrocyte Sedimentation Rate (ESR). Plasma, due to having a lower density, moves to the top while the blood cells precipitate/sediment to the bottom of a sedimentation system. The sedimentation rate (usually defined in terms of mm (drop) per Hour—mm/h) is usually only determined macro-morphologically by measuring the distance from the top cellular level to the top of plasmatic level in a macro-scale sample in a vertical tube or the like.

The measurement of the ESR has clinical relevance in many specific disease processes. It may be useful in predicting prognosis and determining response to treatment in such diseases as rheumatic arthritis, Hodgkin disease, osteomyelitis, and septic arthritis for example. Some other examples of pathophysiological mechanisms which affect the sedimentation rate in blood or other body fluids/materials are acute viral and bacterial infections, chronic inflammations, rheumatoid diseases, tuberculosis, anaemia, malignant diseases (leukaemia, solid tumours), myeloma, congenital heart defects, anaemia and other changes of the red blood cell shape (e.g. sickle cell disease). Hypofibrinogenaemia and certain drugs also affect the sedimentation rate, usually by decreasing sedimentation rate compared to the normal level. The sedimentation test is also of prognostic value and can serve as an index of the relative severity of infection and tissue damage.

Currently, there are several methods that are regularly used to measure the ESR. The three most important and commonly used methods are: Westergren, Rourke and Enrstene, and Wintrobe and Landsberg.

The Westergren method remains the reference standard for measuring the ESR as it is simple, inexpensive, easily available, and accurate; however, the sixty-minute sedimentation time requirement is a disadvantage. Other methods have a faster time to answer, but they are either cumbersome, expensive, or require special equipment. In an emergency department, time and need for rapid disposition is of critical importance and thus should be minimised. Other drawbacks of these methods are, for example: the blood specimen must be properly mixed with the proper anticoagulant to obtain an undiluted representative sample; the test should be set up within two hours after the blood sample is collected to avoid a false low sedimentation rate; any increase/decrease in temperature accelerates/decelerates the rate; and the tube must be vertical—for example, only a three-degree variation from the vertical causes the rate to accelerate by thirty percent.

The invention described here is a micro-sensor and therefore has a very low power requirement and can be realised in a handheld size instrument. Moreover, gyroscopes can be added to the (hand-held) instrumentation to compensate for tilt, for example, even on a desktop the desk may not be ideally horizontal (and so the measurement chamber not vertical). The micro-sensor can also simultaneously measure the volume percentage of cells (i.e. Haematocrit) from calibrated characteristics of the absolute signal, and simultaneously measure temperature of the sample through absolute measurement by means of the integrated movement sensor (e.g. made of a piezo resistive material or metal—hence able to measure temperature directly) and/or heater element resistance, when suitably calibrated with a known temperature coefficient of resistance (TCR).

Accordingly, the measurement devices and methods described herein overcome these drawbacks due to their micro-scale dimensions, portability, sensitivity of the micro-cantilever based sensor, fast time to answer, and allows parallel determination of Haematocrit for sedimentation rate correction and added clinical information.

Figure 3A:
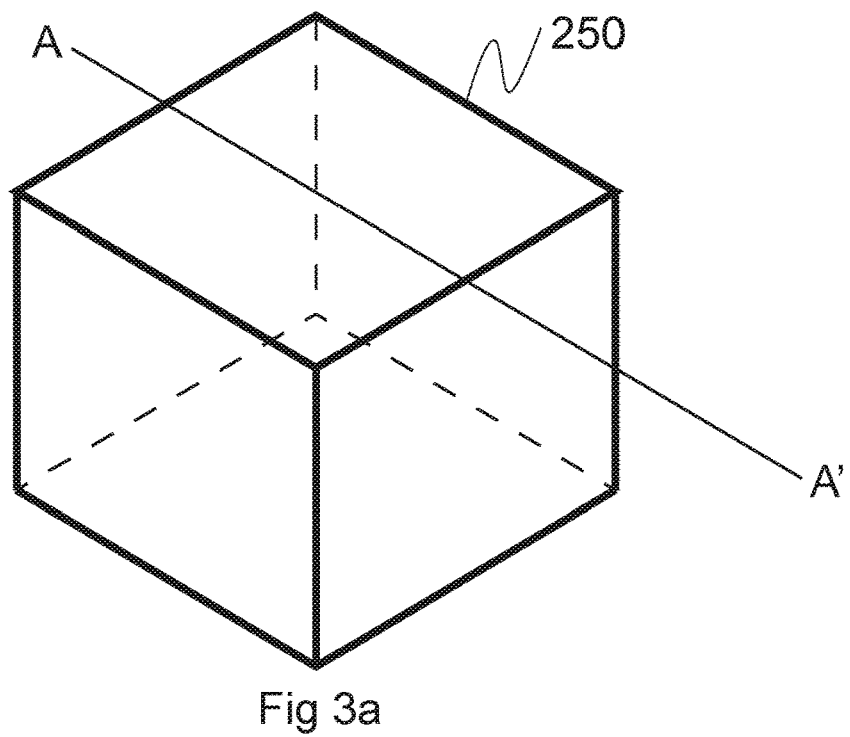
FIG. 3 shows different example potential positions of one or more micro-cantilevers for detecting/measuring sedimentation/buoyancy of suspended particles or rate of diffusion and/or dispersion of particles in suspensions or diffusion in solutions according to examples of the invention.
Figure 3B:
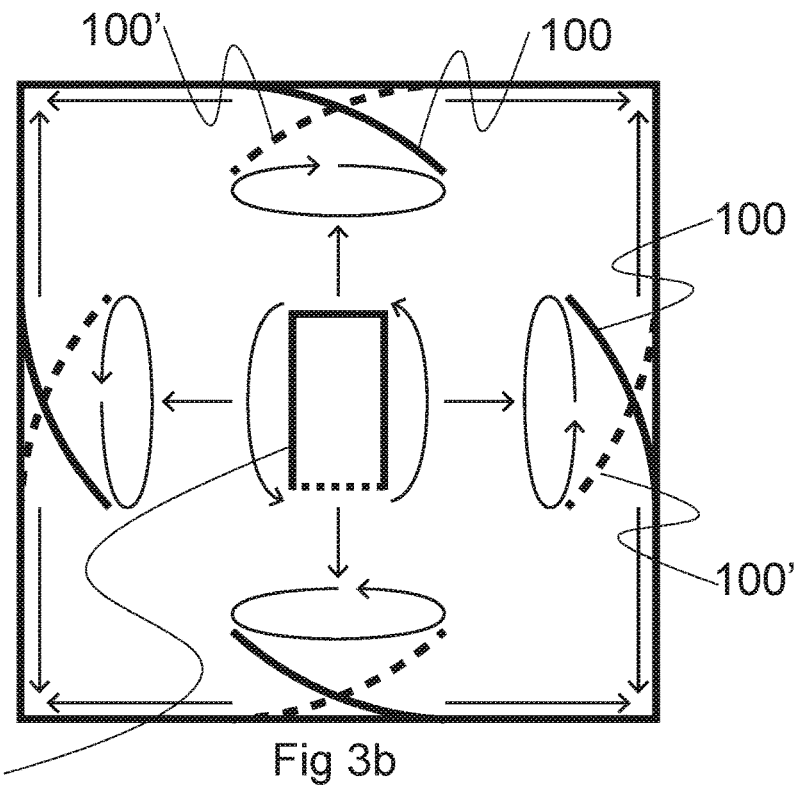

FIGS. 3a and 3b (not to scale) shows different example potential placements (locations) and orientations of the micro-actuator sensors 100 according to embodiments of the invention within a test chamber 250. In the example of these figures, there is FIG. 3a a square box sample test chamber 250 with a cross section between A and A' (i.e. cutting the box in half), and in FIG. 3b, the view looking sideways face on to the cross-section along the line A to A'.

In FIG. 3b, there is shown (in side/edge-on view) in solid line the micro-cantilevers 100 bending inwards from the plane of the inner surface of the test chamber (i.e., in this case, each side (and top and bottom) of the sample test chamber box). There are also shown (in side/edge-on view) in dotted line 100' the potential arrangement of a micro-cantilever with opposite orientation to the solid line (i.e. resultant from a 180 degree turn of the respective micro-cantilever on its respective surface—this rotation being denoted by the arrows in circular formation adjacent each example micro-cantilever). There are also shown vertical/horizontal arrows showing how the micro-cantilevers can be placed anywhere along each plane, and rotation arrows, showing that the micro-cantilevers may be placed at any orientation along a 360 degree turn in the plane of the surface on which the micro-cantilever is placed (where 0 degree is the micro-cantilever at one orientation, and 360 is back at the same orientation, with every other possible orientation angle in between). In the middle of FIG. 3b, there is an example representing a single micro-cantilever viewed from above (with reference to FIG. 1)—this may be an example of a micro-cantilever as though formed on the front or back surface of the test chamber (relative to how the view is shown in this figure). This also shows how the micro-cantilever can be moved anywhere on the plane on which the micro-cantilever is formed, and also shows the ability to rotate the micro-cantilever in any direction.

In summary, the micro-cantilever sensors according to embodiments of the invention may be placed at any position and at any orientation within a sample test chamber on its inner surface. These include, but are not limited to, placement at any suitable position on the top, bottom, or any side of the test chamber, and pointing at any angle. The 'bottom' is the (region) nearest to the lower horizontal plane (i.e. floor) of the test chamber, whilst 'top' denotes the region nearest the upper horizontal plane (i.e. nearest to the ceiling) of the test chamber, thus the sensor being on the "top" is furthest away from the 'bottom'. The terms top, bottom and sides may be made relative to a force acting on the apparatus, for example, the action of gravity or centrifugal force or up-thrust force exerted on particles, since these devices measure sedimentation, buoyancy and/or diffusion, which may be at least partly related to one or other, or any combination of these forces.

The exact placement and orientation of the micro-cantilevers may be related to the desired form of sedimentation or buoyancy wished to be detected. For example, in in-situ measurement embodiments (e.g. placement of one or more, up to a plurality, of the described sedimentation detection micro-cantilevers throughout an entity to be observed, e.g. an engine or industrial process machinery) the micro-cantilever sensors may be placed at positions where detectable results may be expected to be seen. In the example of an engine, this may mean being placed at a lowest point, or at one corner of a lowest point, directly below an aperture from which sedimenting particles, such as particles due to wearing of the engine, may fall.

It will be appreciated that the micro-cantilevers are usually formed to "peel away" from the sample chamber wall, roof or floor (i.e. when placed on sides, top or bottom, respectively), and as such, in a typical example configuration using two sensors with the sensors located at/on either ends or sides of a test chamber (e.g. on opposite side walls, or on top and bottom), the micro-cantilever sensors will be inverted relative to one another. E.g. for an example case where the micro-cantilevers are placed on the top horizontal plane and bottom horizontal plane of a test chamber in the form of a box, then the bottom micro-cantilever may be arranged to peel away upwards from the floor, and hence curl up into the test chamber cavity, whilst the other micro-cantilever located at a top position will peel away downwards from the ceiling, and hence curl down into the test chamber. In this way, a combined measurement device may be able to simultaneously detect any sedimentation and any buoyancy, or rate of diffusion of particles in suspensions or rate of diffusion in solutions. It will be appreciated that the terms "top", "bottom" and "side" are relative terms, with respect to another measure, such as gravity. However, these may equally be seen as being located at either ends of a test chamber, regardless of chamber orientation, as such. Put another way, the sensing portion (e.g. elastic member) is always typically pointing away from the boundaries of the chamber (walls, ceiling, etc.) into the chamber, being fully immersed in the fluid medium sample.

The arrangement of at least two micro-cantilever sensors, for example, with at least one at either end of a test chamber, may be a particularly useful arrangement for sensing both sedimenting portions and portions experiencing buoyancy. For example, this may be a beneficial arrangement in monitoring engine oil life, or the like, because this would enable both the detection of pollutants/particulates that are buoyant in the oil (e.g. chemicals or particulates resulting from the breakdown or reaction of the oil with other chemicals, e.g. water), as well as the measurement of other particles/pollutants that are sedimenting in the oil, such as, for example, bits of worn away metal, or other heavier than oil particles. Such a dual arrangement may be used to determine the level of pollution of engine oil (e.g. from the sedimenting out metallic particles, which in turn is indicative of wear of the engine) whilst at the same time allowing potential measurement of oil quality/lifespan (from the measurement of buoyant particles, that may be derived from the breakdown of oil under action of another agent). It will be appreciated that other use cases exist for a dual buoyancy and/or sedimentation and/or diffusion of particles measurement apparatus in suspensions and colloids, as well as monitoring localised diffusion rates in solutions.

The dual measurement examples may be formed to have more than one sub-portion of the test chamber, with a sensor in each sub-portion, but each sub-portion being in complete fluid communication with the other sub-portions. This is to say, the test chamber may be separated for carrying out the respective tests by each instance of a micro-cantilever, but able to be filled with a fluid medium sample for testing in a single action. The test chamber may be any suitably shaped arrangement, preferably being a test chamber having a substantive vertical portion in which the sedimentation is to take place, and having at least flat surface portions in the area of the micro-cantilevers. Examples include cylinders with flat ends at the top and bottom (or, in the case of a single sensor, at least one flat end at the top or bottom), rectangular or square chambers having flat sides at each ends of each axis, or even shapes having multiple faceted sides, e.g. a dodecahedron, or the like.

The test chamber may be inverted or otherwise rotated in any direction and angle in free space during use, as part of a single test, or to allow multiple tests at different orientations of the test chamber. For example, a test chamber having one or more micro-cantilevers therein may be place at a first orientation, with the output(s) of the at least one micro-cantilever(s) sampled at single point in time (or over a pre-determined time period), then the test chamber may be inverted and the output(s) of the same or different micro-cantilever(s) of the (re-)sampled at a second point in time, or over a second suitable predetermined time period. For example, there may be provided a dual chambered device (potentially with fluid communication between the two chambers, for filling with the fluid medium sample under test), with a sensor at a respective end of each chamber, that can test for buoyancy and sedimentation on the (set of) fluid samples at the same time, optionally using a single flip of the overall sedimentation measurement apparatus to allow double testing, to thereby achieve an average result. Such an arrangement may have a single sensor in each chamber, diametrically opposite one another (i.e. two micro-cantilever sensors in total), or it may further include a micro-cantilever sensor at each end of both chambers (i.e. four micro-cantilever sensors in total).

Figure 4:
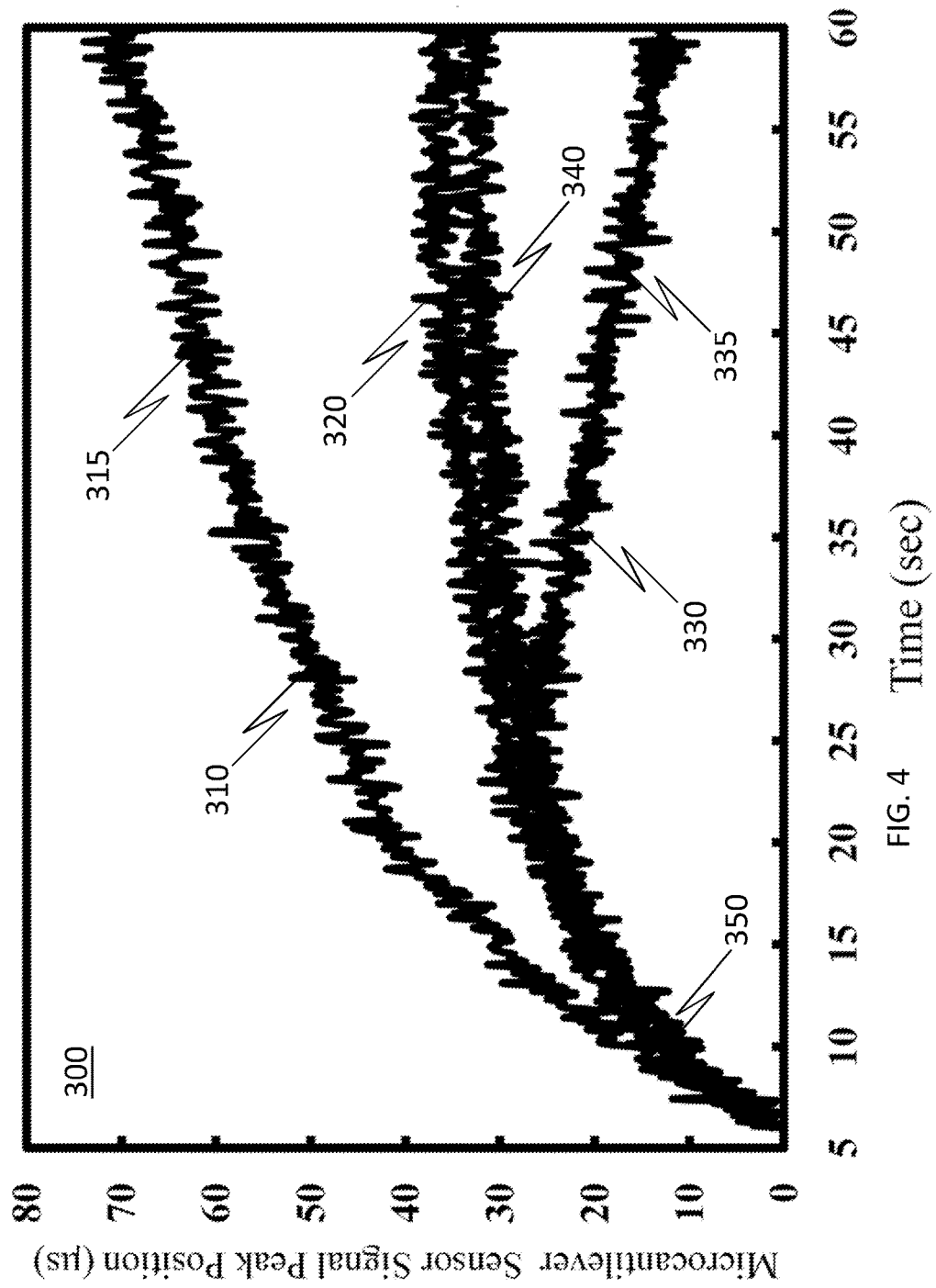
FIG. 4 shows an output signal from a micro-cantilever sensor according to an example embodiment of the invention for a response to sedimentation of red blood cells in whole blood under different orientations with comparison to a plasma fluid sample.

It will also be appreciated that multiple micro-cantilevers may be placed across an area of the inner surface of the test chamber, for example on the sides (i.e. walls) or top and bottom of the test chamber, thereby providing a capability to determine relative sedimentation or buoyancy rates across a selected area or volume of the test chamber. FIG. 4 shows the electrical response 300 of the micro-cantilever piezo-resistor based sensor during actuation of the at least one micro-heater 140, when the micro-cantilever is located at the bottom of the measurement chamber (i.e. bending up and out of the horizontal plane) where the fluid medium sample is Citrated Whole Blood (plot 310) and Plasma (plot 320) respectively. Meanwhile, FIG. 4 also shows similar plots for the same type of micro-cantilever sedimentation sensor when it is located at the top of the sample chamber (i.e. bending downwards and out of the horizontal plane) for the cases of Citrated Whole Blood (plot 330) and Plasma (plot 340) fluid samples. In all cases of this example, the micro-cantilever is actuated at 10 Hz with a pulse width of 0.5 ms and 6V. However, other actuation signal values may be used.

Each data point in the plotted graphs of FIG. 4 represents a single pulse, wherein the maximum position of micro-cantilever movement response relative to the falling edge (off) of the actuation signal is measured and compared to the first data point measured at 4 seconds (in this example, but other times may be used) after the sample has initiated the test. No referencing using a second micro-cantilever in a half bridge or full Wheatstone bridge configuration or analytical background reduction of the data has been implemented in this example, but can be used if desired. In this set of test examples, the active measurement chamber has 400 microns height, 600 microns width, and 1000 microns length, thus equating to 240 nano-liters volume. However, other suitable chamber size parameters may be used.

From this set of plots, it can be seen that in both orientations (i.e. sensor at top, or bottom, respectively), the response for the plasma fluid sample is largely unaffected (there is minor change, but this would be removed through calibration) as there are no red cells present in the system, and so there is no sedimentation possible. Meanwhile, in whole blood, the sedimentation of red cells is measured as a definite and measurable increase in the output signal 315 where red cells move towards the sensor and decrease in signal 335 where cells move away from the sensor. All responses include the initial settling of the sensor system 350 which can be removed analytically or using a reference micro-cantilever sensor in a half or full Wheatstone bridge configuration. Given the size of the sample chamber for the fluid sample (in this case, whole blood or plasma, respectively), FIG. 4 shows the measurement of red cell sedimentation on a sub-microliter measurement chamber.

In the described examples, it is the peak position of the output signal that is being tracked, therefore the more damping experienced, the more the peak position increases. Hence, the graphs in the figures show a signal that looks as though it is increasing, but the actual physical circumstances are that the amplitude and the sweeping motion is decreasing.

The response under opposite orientation (i.e. with the sensor at the top of the chamber) shows the ability of the micro-cantilever sedimentation sensing apparatus according to embodiments of the invention to also measure suspensions rising in a fluid medium (i.e. diffusion and/or dispersion—rate, or extent, etc) due to buoyancy, i.e. particles having a density lower than the bulk fluid medium. These sorts of buoyant particles could be a result of suspensions being released from the lower substrate due to/under control of a reaction that detaches the suspensions from a surface, or that opens a chamber containing buoyant suspensions. The measurement of the diffusion and/or dispersion rate of these suspensions allows determination of the reaction occurring and strength/rate of the reaction. The diffusion and/or dispersion rate may be the indirect measure of how quickly a reaction is taking place and/or an indirect measure of whether the particles are being released (or trapped—as opposite to released). Hence, by detecting any changes in the buoyancy and/or sedimentation and/or diffusion of a sample as a whole, it will be possible to monitor or establish the diffusion and dispersion of particles rates.

Figure 5:
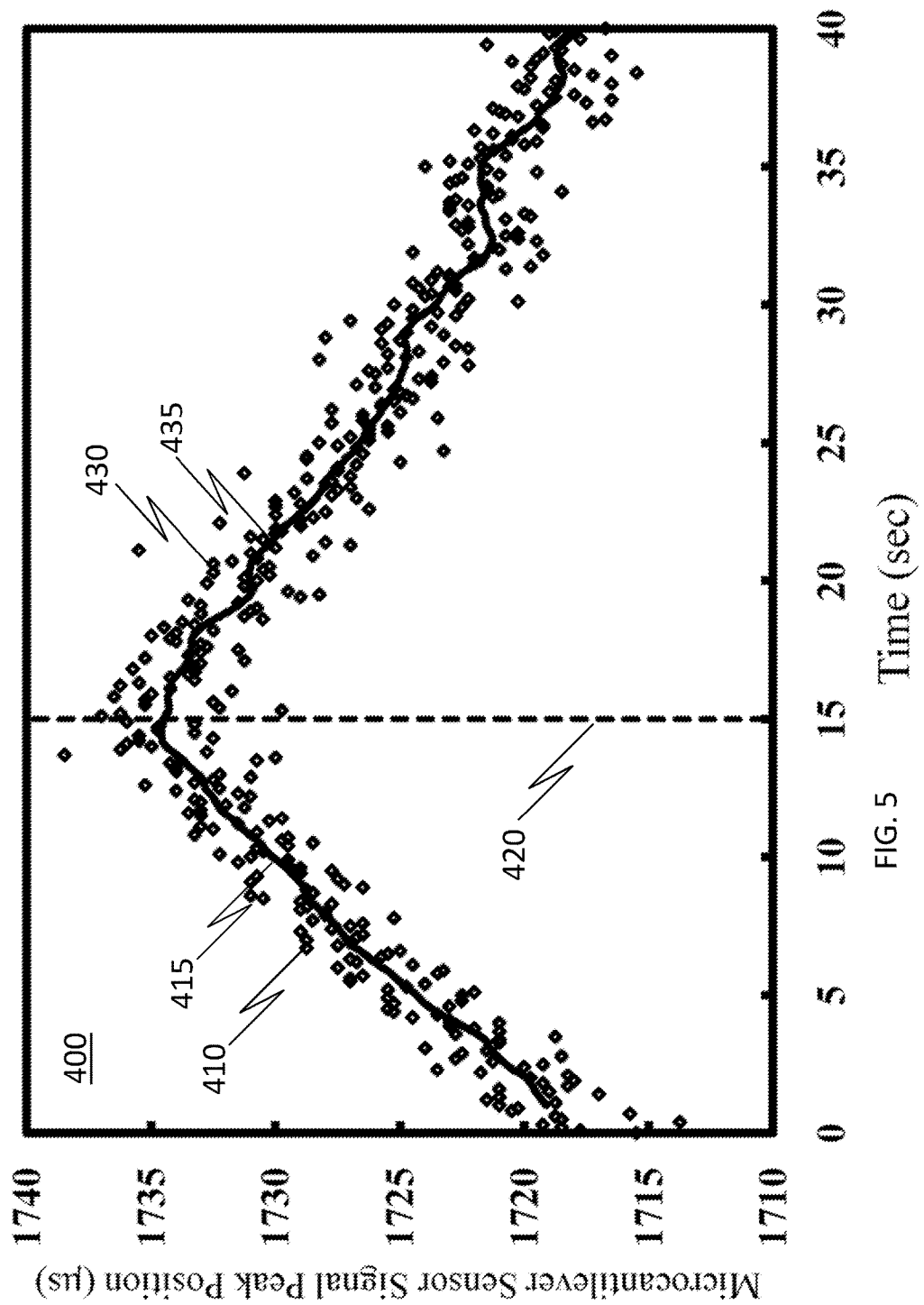
FIG. 5 shows an output signal from a micro-cantilever sensor according to an embodiment of the invention for a response to sedimentation of red blood cells in whole blood before and immediately after inversion.

FIG. 5 shows an example immediate response 400 to the measurement of sedimentation rate of red blood cells in a plasma fluid medium of the micro-cantilever sensor when the whole system is inverted 420, i.e. turned upside down. In this example, the micro-cantilever is again actuated at 10 Hz with a pulse width of 0.5 ms and 6V, but other actuation signal values may be used in other embodiments. Again, each data point represents a single pulse wherein the maximum position of response relative to the falling edge (off) of the actuation is measured. The sensor response 410 is shown where the micro-cantilever sensor is at the bottom of the measurement chamber and the cells move towards the sensor and the sensor response 430 is shown after inversion where the micro-cantilever sensor is at the top of the measurement chamber and the cells move away from the sensor. A rolling average of the data before 415 and after inversion 435 is also shown. The active measurement chamber has 400 microns height, 600 microns width, and 1000 microns length equal to 240 nano-liters volume. No referencing using a second micro-cantilever in a half bridge or full Wheatstone bridge configuration or analytical background reduction of the data has been implemented.

It has also been reported that Haematocrit (cell volume percentage of a specimen of blood) has an important effect on the rate of sedimentation of the red blood cells, because it is believed that the higher the cell volume percentage, the slower the sedimentation rate; and the lower the cell volume percentage, the faster the rate. Therefore, known methods of measuring ESR without compensation may be inaccurate in this respect.

There are several pathologies where parallel measurement of Haematocrit and sedimentation has clinical utility. The Haematocrit value is also the most useful single index for determining the degree of anaemia or polycythaemia, because it can be the most accurate (2-4 percent error) of all haematological determinations. In contrast, the direct red blood cell chamber count test methodology has a percent error of 8-10 percent. The Haematocrit test is, therefore, preferable to the red blood cell count as a screening test for anaemia. The values for the Haematocrit test closely parallel the values for the haemoglobin and red blood cell count. Since both anaemia and infection can accelerate the rate of sedimentation, a correction may be made for the influence of anaemia before the sedimentation test can be used as an accurate index of the severity of infection. Usefully, embodiments of the present invention can additionally make a Haematocrit determination in parallel with the measurement of the sedimentation rate.

The need for a more accurate method for correcting sedimentation rate for variations in cell volume percentage is apparent to increase the value of a sedimentation rate test. The value of the sedimentation test as an index of the severity of infection or tissue damage in the body is greatly increased if a correction is made for the effect of variations in cell volume percentage. Thus embodiments of the present invention provide an even further improved sedimentation (rate or level of) testing apparatus.

Figure 6:
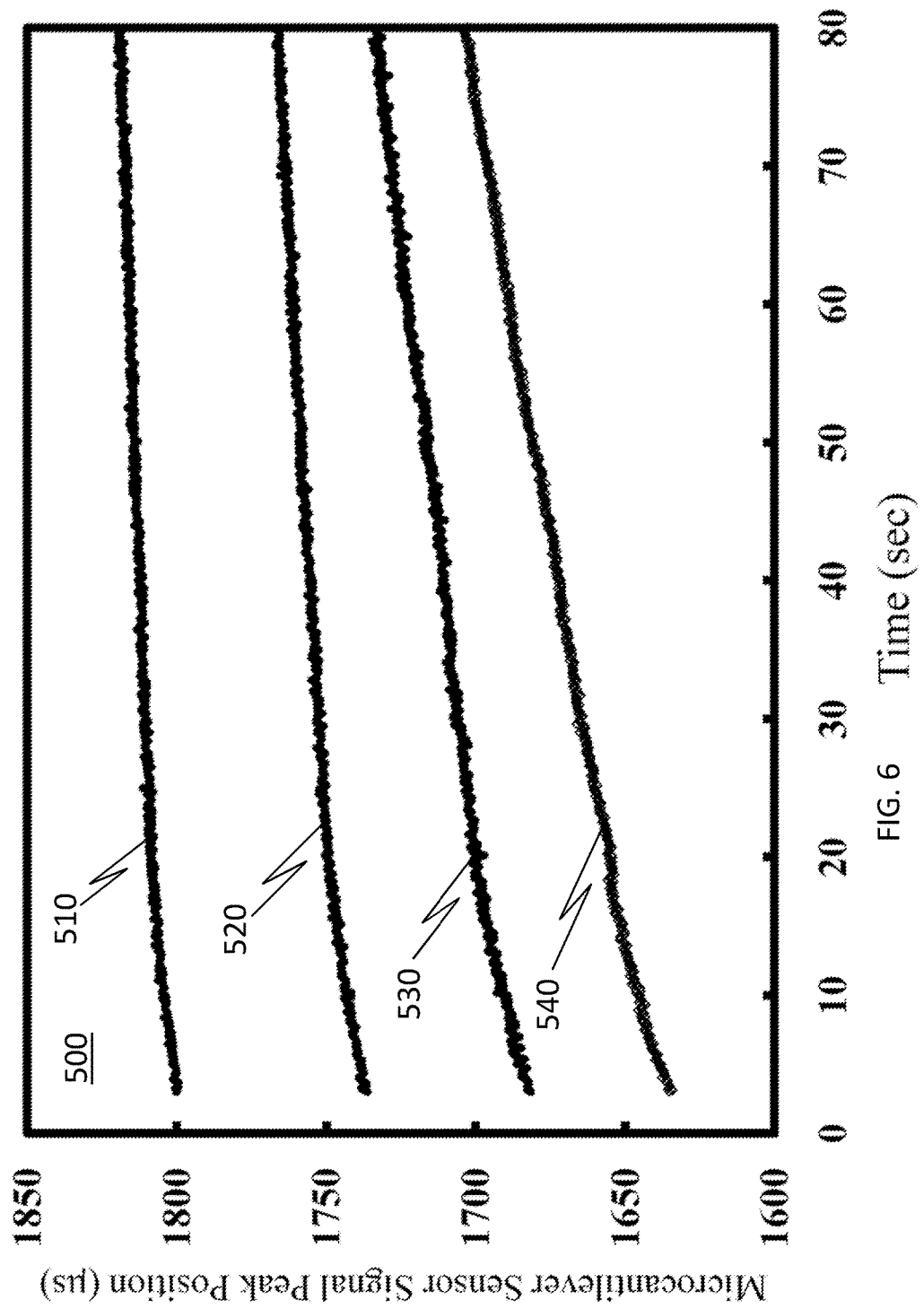
FIG. 6 shows an output signal from a micro-cantilever sensor according to an example embodiment of the invention for a calibrated response to various Haematocrit (cell volume percentage of a specimen of blood) levels in whole blood.

FIG. 6 shows the electrical response of the piezo-resistor sensor within an example micro-cantilever sedimentation sensor according to embodiments of the invention during actuation of the micro-heater 140, when the micro-cantilever is located at the bottom of the measurement chamber in Citrated Whole Blood with various Haematocrit 500. In this example, the micro-cantilever is actuated at 10 Hz with a pulse width of 0.5 ms and 6V, but other actuation signals values may be used in alternative examples. Again, each data point represents a single pulse wherein the maximum position of response relative to the falling edge (off) of the actuation is measured, and no referencing using a second micro-cantilever in a half bridge or full Wheatstone bridge configuration or analytical background reduction of the data has been implemented. Again, the active measurement chamber has 400 microns height, 600 microns width, and 1000 microns length, equaling 240 nano-liters in volume. FIG. 6 shows four distinct traces, each being the response from citrated whole blood with (different) volume percentage of red cells, or Haematocrit, of 60% 510, 50% 520, 40% 530, and 30% 540. Thus, for samples that can experience sedimentation, the distinct separation of initial Peak Position allows for parallel and simultaneous determination of Haematocrit in the sample, together with the sedimentation. This is because, when combined with the information in FIG. 4, it can be seen that the sedimentation is measured as a direction of ascending or descending peak position, whilst the Haematocrit value is the initial starting point of said peak position.

Figure 7:
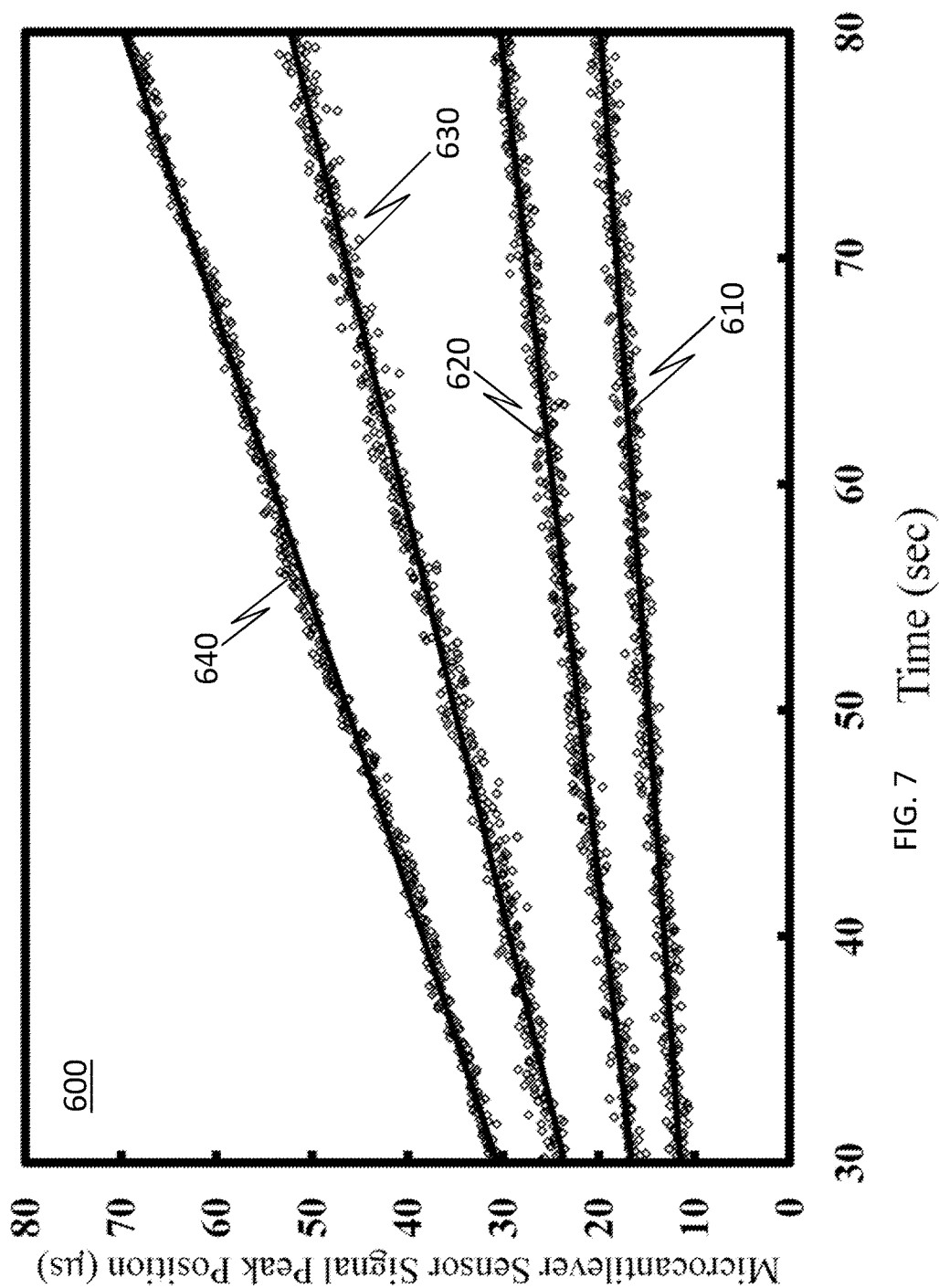
FIG. 7 shows an output signal from a micro-cantilever sensor according to an example embodiment of the invention for a response to various Haematocrit (cell volume percentage of a specimen of blood) levels in whole blood.

FIG. 7 shows the section from 30-80 seconds in the test from FIG. 6 (but where all the graphs are normalised to start from Y=0 at time, t=0) for the electrical responses 600 of the micro-cantilever sedimentation measurement apparatus having haematocrit calibration according to example embodiments of the present invention, in various sedimentation samples having different haematocrit values, thus showing this dual measurement capability (or rather, the ability to measure one parameter—the sedimentation, whilst being calibrated for the other—haematocrit). Each data point represents a single pulse wherein the maximum position of response relative to the falling edge (off) of the actuation is measured and compared to the first data point measured at 4 seconds after the sample has initiated the test.

FIG. 7 shows four distinct responses with linear fit from citrated whole blood with volume percentage of red cells, or Haematocrit, of 60% 610, 50% 620, 40% 630, and 30% 640.

Whilst examples of the present invention are very sensitive to these sedimentation and haematocrit parameters/relative changes in these parameters, it will be appreciated that absolute value measurements for these parameters may need calibration against known values to provide nominal output values, comparable to the results from other methods.

The accuracy of the described Haematocrit measurement may also be improved by obtaining values for/accounting for resistance of the micro-cantilever piezo-resistor and/or micro-heater resistance, as well as filter and gain calibration of the instrumentation, environmental temperature and humidity, and sample temperature. These may be calibrated, for example, by measuring the peak position and peak amplitude of the micro-cantilever signal under fixed environment conditions and then under controlled changes in environment, essentially providing a look-up table or equation to correct intrinsically for the signal.

The afore-described sedimentation measurement device may form part of a dynamic micro test/diagnostic system that is sensitive to the measurement of sedimentation rate or diffusion rate of suspensions or precipitants of one or more specified reactions in a fluid medium sample, over time, and with varying haematocrit values. The specified reaction under test could be, for example, an immuno-precipitation reaction. Immuno-precipitation is a method that uses the principle of antigen-antibody reaction for qualitative or quantitative detection of an analyte. Immuno-precipitation involves the interaction between a protein and its specific antibody, the separation of these immune complexes and the subsequent analysis by for example SDS-PAGE. This technique provides a means to separate a specific protein from a sample, e.g. whole cell lysates or culture supernatants. Additionally, one can use immuno-precipitation to confirm the identity of or study biochemical characteristics, post-translational modifications, and expression levels of a protein of interest. Traditionally the procedure can be divided into several stages: Sample preparation; Pre-clearing; Antibody incubation/formation of antibody-antigen complexes; Precipitation; and Analysis by Sodium Dodecyl Sulfate-PolyAcrylamide Gel Electrophoresis (SDS-PAGE).

The immuno-precipitation technique requires the precipitation of a protein out of solution using an antibody that specifically binds to that particular protein, and this process can be used to isolate and concentrate a particular protein from a sample containing many thousands of different other proteins. Immuno-precipitation requires that the antibody be coupled to a solid substrate at some point in the procedure. Historically the solid-phase support for immuno-precipitation used by the majority of scientists has been highly-porous agarose beads but it has been found that in embodiments of the invention, magnetic beads may be used as an alternative to agarose beads as the solid substrate. This is due to the magnetic beads having high efficiency, specificity, reproducibility simplicity (no centrifugation, less incubation time and reduced washing steps, no pre-clearing step, easy visualization of the magnetic nanoparticles), minimal loss of protein and stress compared to centrifugation, flexibility and greater surface area to volume ratio for optimum antibody binding.

Therefore magnetic beads are an ideal solid surface system, as they exhibit similar binding capacities and other physical characteristics to the traditionally used agarose beads but present other benefits such as simplicity of handling, no need of equipment such as centrifuges, their paramagnetic properties make them ideal for rapid assays and their consistent size, shape and performance.

Any solid surface method to bind and detect binding may be used in examples of the invention. Also, examples may work with any form of beads, as long as they are dense or large enough to promote sedimentation after binding (e.g. gold sol particles), for the case of sedimentation detection, or buoyant enough in the case of buoyancy detection, or, indirect measurement of dissolution of particle binding agent (coating) as a result of which the suspension sample characteristics change (e.g. enhancing or suppressing buoyancy or sedimentation).

Moreover, in some embodiments, magnetic beads for example are used as functionalised carriers and therefore will sediment if the reaction that takes place allows for aggregation or grouping or the like, thereby potentially accelerating the sedimentation or buoyancy (or their rate) Also, the symbiotic nature of the integration of particles may allow for better diagnostic methods Tests where sedimentation or precipitation occur can be measured because of the properties and sensitivity of the micro-sensor as well as the reduced dimensions of the reaction chamber to detect precipitation of cells, particles (latex, magnetic and the like) bound or un-bound to biomolecules (e.g. antibodies).

Embodiments of the present invention may also be used as a form of sedimentation switch (i.e. activates on reaching a certain level of sedimentation). This may particularly be done using a micro-cantilever that is arranged to be pre-bent, out of the plane, at ambient temperature, so that when particles sediment out, they force the micro-cantilever downwards. The micro-cantilever may be pulsed to "test" the level of sedimentation, e.g. to see who much heat generation (related to amount of energy imparted into the heater) is required to move the micro-cantilever, at all, or a predetermined amount, thus helping to define/determine the sedimentation level, and when used over time, the rate of sedimentation. Use of a micro-cantilever in an inverted position and/or orientation may allow a buoyancy switch in much the same way.

Examples of the invention may use the above-described sensor capability, combined with the basic principles of sedimentation and precipitation, to measure binding between biomolecules (for example by immuno-precipitation) through measurement of the sedimentation rate of precipitants. The simplicity, high sensitivity, flexibility and fast kinetics of the micro-cantilever based sedimentation sensor may be combined with the principle of antibody—antigen binding and the ability of the micro-cantilever to detect precipitation of cells, particles or complexes through sedimentation or diffusion rate of said precipitants with great sensitivity.

Normally immuno-precipitation testing protocols involve several steps performed by highly trained scientists. By using the above-described capabilities of the micro-cantilever sedimentation sensor according to example embodiments of the invention (sensitivity, small reaction chamber dimensions, etc.), the immuno-precipitation testing process will be faster and may be performed in one step from sample application to binding and detection, and without the need for highly trained test personnel. For example, the antigen will bind to the antibody that is (pre-)attached to particles (e.g. magnetic or agarose beads) in the reaction area and because of the density of the attached particles and the size of the immuno-complex, the bound material will precipitate and this event will be detected by the sensor, as described above in FIGS. 4 and 7, while any non-specific un-bound material may be washed away using a fluid flow, in the case where the sedimentation detecting micro-cantilever(s) is/are formed on a surface of an in-line processing flow system—e.g. a pipe of foodstuffs in a food factory, a fuel or oil line or the like. The signal generated from the described micro-cantilever based sedimentation apparatus may be isolated and modulated by using different sizes of particles, antibodies specific to the target analyte and also non-specific antibodies (i.e. which will not bind the target analyte) for background measurements, different channels and reactions areas to create reference sensors, signal subtraction, etc.

Embodiments of the present invention may also provide a measurement device and method for the measurement of diffusion or perfusion rate across membranes and the like. This is because concentration gradients can drive diffusion of ions, molecules or blood cells through blood capillary walls, therefore in some examples, multiple sensors may be used to allow sequential measurement of capillary blood samples, which can give an indication of cellular diffusion rates, which in turn may prove useful in assessment of causes, such as erythrocyte dehydration in conditions such as sickle cell disease and the like. One or more micro-cantilever based sedimentation sensors, each under different orientation in the bulk fluid medium sample, may be used to measure the diffusion rate through the fluid sample and therefore indicate the diffusion or perfusion rate across membranes, and the like, whilst still having the advantages of simplicity, high sensitivity, flexibility and fast kinetics of the sensors relative to other sedimentation measurement methods and apparatuses.

The term 'fluid medium sample' is used herein to generally mean a smaller (size) sample of a general 'fluid medium' under test, and may imply a sort of "in vitro" testing of that fluid medium, i.e., a test of a sample of the fluid medium in a testing chamber of a dedicated sedimentation testing device incorporating the micro-cantilever based sedimentation sensor described herein. Such a testing device may, for example, take the form of a hand-held electronic device having a fluid medium sample containing test chamber with the at least one micro-cantilever located therein, a more particular example being a blood testing device. However, it will be appreciated that the sedimentation devices disclosed and described in detail herein may also be placed within a larger entity having vital fluids for operation, e.g. an engine with its lubricating oils, or a fluid inherent within, such as in the case of a brewing manufacturing line. In these "macro" situations, the fluid medium is not a sample per se, but just the fluid medium in general use. In this sort of situation, the micro-cantilever based sedimentation sensors may be located within and around the entity under sedimentation observation (such as an engine or industrial manufacturing process line, e.g. commercial brewing apparatus or the like) so that they may monitor the (potential) changes in the fluid medium, including existence, extent or other parameter of sedimentation. For example, an engine may have a plurality of described sedimentation sensors distributed around its oil lubrication supply system, to thereby monitor the lubricant.

Figure 8:
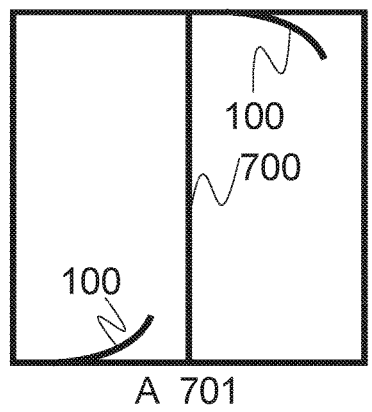
FIG. 8 shows some dual or more chambered example embodiments of the invention, with different numbers and locations of micro-cantilevers.
Figure 8:
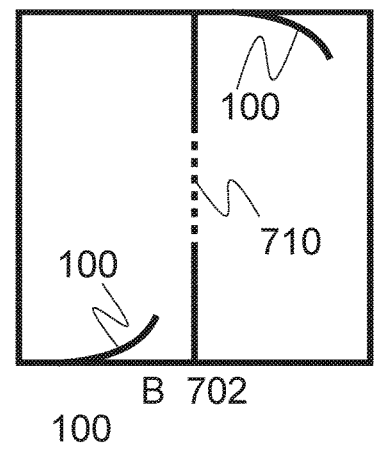
Figure 8:
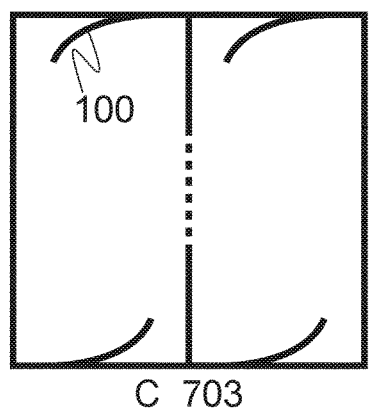
Figure 8:
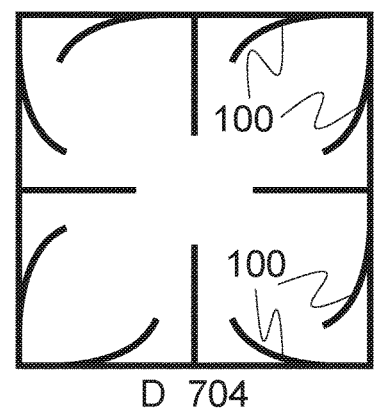
Figure 8:
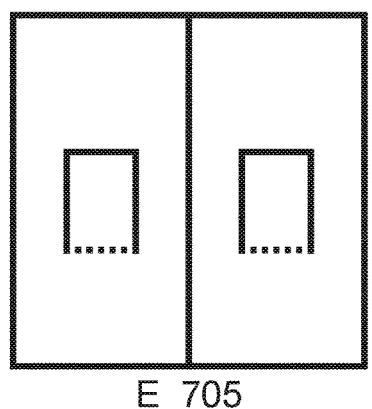
Figure 8:
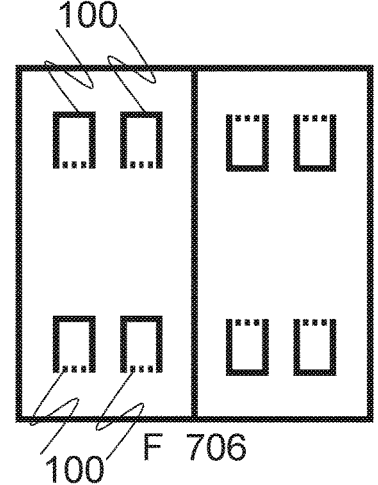

FIG. 8 shows a number of example multi chambered example arrangements according to embodiments of the invention. In all cases, these are viewed as a cross-section, similar to as represented in FIGS. 3a/b. In particular there are shown the examples of:

A 701—a dual chamber without fluid communication between the two chambers (indicated by solid partitioning line 700) with micro-cantilevers at diametrically opposite ends of the overall test chamber (in this case formed of two portions), and with each micro-cantilever being inverted relative to the other.

B 702—similar to A, except the dual test chamber is in fluid communication, indicated by the dashed portion 710 of the separator line in the middle of the figure.

C 703—similar to A and B, except there at least four micro-cantilevers, arrange so that there is one per end of the two chambers;

D 704—this time there are at least four chambers, each with two micro0cantilevers at different orientations;

E 705—this shows the same apparatus as C, but viewed from the top or bottom of figure C, showing, in this example, that there is one micro-cantilever per section/chamber end, in the middle of the respect (sub-) chamber end.

F 706—This shows an enlarged version of Fig C 703, in which there is now a grid of four micro-cantilevers in each section/chamber end. This figure also shows the orientation of the micro-cantilevers in one chamber can be different to those in another chamber. The micro-cantilevers may also be in different orientations within the same chamber, as desired.

Directionality of bending/curling—the micro-cantilevers may be formed to bend in either direction when the actuating heat is applied—in the forgoing example embodiments, the micro-cantilever(s) are formed such that they bend up, out of plane, when located on the bottom horizontal plane of the test chamber and a single is applied, and drop back into plane as the actuating signal is removed, and the heat generated dissipated away. Equally, where the micro-cantilever sensors are located at/on the top horizontal plane of the test chamber, and therefore are inverted relative to a bottom location, they will bend down, out of plane on application of an actuating signal, and "drop back" i.e. bend up back into the plane when the heat from the actuation signal dissipates.

Embodiments described above include a method and apparatus for active differential sensing of reactions in a fluid medium sample under test using two or more micro-cantilevers, i.e. one that actuates both first and second micro-cantilevers simultaneously. When activating in this way both responses (i.e. the output signal) of the respective micro-cantilevers have a signal and background noise, and the described differential method is then "a measure of the difference between two active signals". This is in contrast to previous differential methods that do not activate one of the micro-cantilever sensors in a differential test, i.e. what we may call passive differential test, or "a measure of the difference between one active signal and background noise". This difference between the active differential sensing described above, and the known passive differential sensing may be best illustrated mathematically (for the case of two micro-sensors, but can be extrapolated up to any number of micro-cantilevers, accordingly) as:

Passive differential sensing=(SIG $A$+ DRIFT)$_{cantilever1}$−(DRIFT)$_{cantilever2}$=(SIG $A$)

Whereas the above described active differential embodiments the invention=(SIG A+DRIFT)$_{cantilever1}$−(SIG B+DRIFT)$_{cantilever2}$=(SIG A−SIG B), Where DRIFT is the background noise induced drift in responses between the two identical (other than, for example, positioning—e.g. placement of the micro-cantilevers at the top/bottom/sides of a sample chamber, as described in more detail above with respect to FIG. 3) micro-cantilevers. Thus, the above described active differential method may be a true differential measure of the different sensor outputs. In such a way, the active differential sensing method may be used, for example, to allow the tracking of the progress of a reaction or similar through detecting the sedimentation (or rate and/or buoyancy (rate), and other parameters of sedimentation or buoyancy influencing diffusion and/or dispersion of particles described herein. This may be done in particular where the micro-cantilevers according to embodiments of the present invention are located within, or on a surface of, a greater (i.e. larger) sized vessel, e.g. a production vat or vessel, containing (a macro-sample) of the one or more fluids under test (including reagent, where applicable), and those micro-cantilevers are formed in an array or physical selection of locations around or within the vessel, so that the outputs of each sensor can be compared directly, without drift, and therefore are able to track the "wave front" of a moving reaction. Alternatively, these arrays can simply detect where final fully mixed/fully reacted portions of the fluid medium sample are located, relative to portions where the reaction is still yet to occur, or complete. This is because each micro-cantilever is substantially identical (through identical mass production on the same wafer), and by using the active differential comparison method described above, it allows, for example, comparing the output of a cantilever at the very bottom of a production vat of some mixture (including multiple base fluids and reagents, as appropriate for the respective production) with the very top where the (latest) substance was added—e.g. in the production of mayonnaise, the addition of oil to egg yolks. Here a suitably formed and positioned array (of any suitable number) of micro-cantilevers arranged to carry out the differential sensing method would allow the progress of the emulsification of the oil with/by/into the egg yolk to be tracked. This clearly may be applied to any process in which a change in physical properties of a medium can be useful in knowing when the process is complete, not over worked, etc—especially industrial processes that are otherwise more difficult to assess in real-time).

The shape of the array of micro-cantilevers may also help for a particular use case—for example, where the spread of a reaction is needed to be tracked across an area, the array may be formed such that it is in the general form of a set of points in, for example, concentric rings around the reagent entry point.

The output signal(s) of the at least one micro-cantilever(s) may be sampled at any point after the electrical pulse (to heat the integrated heater of the micro-cantilever) has been applied, dependent on requirements of the test.

The apparatus disclosed herein may include suitable electronic logic circuit means for applying the relevant signals to the heater(s) in the micro-cantilevers, and to sample to output signals of the movement/temperature sensors embedded within or on the micro-cantilevers, for example vi the Wheatstone bridge arrangement. The apparatus may further comprise processing logic arranged to process the input and output signals to thereby provide results and/or indications of sedimentation parameters, such as rate and the like, either directly, or after calibration from pre-use, or from prior use in controlled environments. The pre/prior-use control environments may include environments with known parameters, for example, but not limited to sedimentation values, haematocrit values and the like. Memory means, such as Static Random Access Memory (SRAM), flash RAM, or any other suitable storage technology may be incorporated into the overall apparatus, and operatively coupled to the processing logic, so that it may be used to hold the calibration data from the control environments or the like (i.e. calibration data from use of a substantially identical micro-cantilever in a known fluid sample environment, thereby allowing the proper determination of sedimentation in an unknown fluid medium environment).

Note the different micro-cantilevers described in any embodiment above, especially the differential sensing embodiments, may have any of: different coatings applied to each micro-cantilever, the same coating applied to both/all micro-cantilevers, or no coatings applied to either/all micro-cantilevers. The different coating regimes may occur, for example, because:

For use cases where no coatings are applied, this means only the fluid (mixture) under test itself is being analysed, and not any form of reaction based upon the coating(s)—this is particularly useful where the fluid under test can be/needs to be spiked with a reagent at a certain point in time, and the whole of the test results, from before spiking, through spiking itself, to 'end steady state' (where applicable) after spiking can be detected, analysed and the results monitored.

For use cases where different coatings may be applied, for example different reactionary tests can be carried out in the same bulk fluid (e.g. to provide different reagent based reaction comparative testing). For example, a first cantilever may be coated with a first reagent in order to apply a first reagent based test, to determine a first parameter about the bulk fluid under test from the subsequently detected sedimentation or buoyancy parameters, then a second cantilever may be coated with a second reagent in order to apply a second reagent based test, to determine a second parameter about the bulk fluid under test, from still further subsequently detected sedimentation and/or buoyancy parameters. This may be extrapolated up to any suitable number of individual tests involving different coatings of different cantilevers.

The micro-cantilevers may take a number of different shapes, and may include a paddle portion at the far end of the respective micro-cantilevers (i.e. at the end that moves), the paddle portion being of any suitable pre-determined shape and size, dependent upon a desired effect (e.g. amount of drag in the fluid under test, or the like), and also may include one or more apertures between the two sub-portions of the micro-cantilever (as shown in FIG. 1—which in this case shows a single slit along the length of the micro-cantilever).

Nothing in this description is to be taken as limiting the examples, embodiments or claims to only the described selection of features as currently claimed and other selections of features are also contemplated, but not listed out in full, in order to not obscure the description or claims of the invention. Thus, the order and claim numbering is not to be construed as a limitation as to the feature selection and combination, unless said feature combination is a physical impossibility. As may be appreciated, different feature selections may have different synergistic effects that lead to useful and important diagnostic or monitoring abilities, and those combinations have also been contemplated, but not listed out in full to avoid confusion.

The invention claimed is:

1. A method of measuring a sedimentation parameter of suspensions or precipitants in a fluid medium sample, said method comprising:
providing at least one micro-cantilever sensor in the fluid medium sample, said micro-cantilever sensor comprising at least two materials having different coefficients of thermal expansion, and having a heater and piezoresistive sensor integrated therein;
calibrating at least one micro-cantilever response to a percentage cell volume of suspension in the fluid medium sample in known standards to form a calibrated micro-cantilever response characteristic;
pulsing the heater with one or more electrical pulses to induce heat generation in the micro-cantilever;

sampling the output of the integrated piezo-resistive sensor to characterise a response of the micro-cantilever during sedimentation in the fluid medium sample;
determining a value of the sedimentation parameter from the characterised response;
measuring temperature of the fluid medium sample using the micro-cantilever simultaneously with determining the value of the sedimentation parameter; and
correcting the determined value of the sedimentation parameter based on the measured temperature and the calibrated micro-cantilever response characteristic.

2. The method of claim 1, further comprising determining the existence or extent of a predetermined reaction in the fluid medium sample from the determined value of the sedimentation parameter.

3. The method of claim 1, further comprising determining a percentage cell volume of suspension in the fluid medium sample.

4. The method of claim 1, wherein the known standard is a haematocrit standard.

5. The method of claim 2, wherein the fluid medium sample comprises a biological sample, and the reaction includes any one or more of an erythrocyte sedimentation rate and an immuno-precipitation reaction that incorporates the determined value of the sedimentation parameter.

6. The method of claim 1, wherein the sedimentation parameter of the suspensions or the precipitants comprises any one of:
a rate of sedimentation;
an existence or not of sedimentation;
a predetermined amount of sedimentation;
a nominal absolute value of sedimentation;
a suspension concentration; and
haematocrit value.

7. The method of claim 1, wherein the sedimentation parameter of the suspensions or the precipitants is due to the product of, or directly due to, one or more reactions.

8. The method of claim 1, wherein the sedimentation parameter of the suspensions or the precipitants is due to the product of, or directly due to, the action of a flocking agent.

9. The method of claim 1, further comprising measuring, based upon the measured sedimentation parameter, any one or more of: diffusion or perfusion rate of ions, molecules or cells across membranes within the fluid medium sample, diffusion of the suspensions or the precipitants that detach from a surface within the fluid medium sample due to a lower density than the fluid medium, or cellular adhesion to bio-molecules within the fluid medium sample.

10. The method of claim 1, wherein the at least one micro-cantilever sensor comprises a plurality of micro-cantilevers, wherein the plurality of micro-cantilevers are physically distributed along an axis along which the sedimentation acts.

11. The method of claim 1, further comprising:
inverting the at least one micro-cantilevers;
re-pulsing the heater with one or more electrical pulses to induce heat generation in the micro-cantilever;
re-sampling the output of the integrated piezo-resistive sensor to characterise an inverted response of the micro-cantilever during sedimentation in the fluid medium sample; and
determining a value of the sedimentation parameter from the characterised inverted response.

12. A method of measuring a sedimentation parameter of suspensions or precipitants in a fluid medium sample, said method comprising:
providing at least one micro-cantilever sensor in the fluid medium sample, said micro-cantilever sensor comprising at least two materials having different coefficients of thermal expansion, and having a heater and piezo-resistive sensor integrated therein;
pulsing the heater with one or more electrical pulses to induce heat generation in the micro-cantilever;
sampling the output of the integrated piezo-resistive sensor to characterise a response of the micro-cantilever during sedimentation in the fluid medium sample; and
determining a value of the sedimentation parameter from the characterised response
wherein the method further comprises:
measuring temperature of the fluid medium sample using the micro-cantilever simultaneously with determining the value of the sedimentation parameter; and
correcting the determined value of the sedimentation parameter based on the measured temperature, and
wherein the at least one or more micro-cantilever sensors are physically distributed within the fluid medium sample to gain location specific monitoring of sedimentation values.

13. A method of measuring a sedimentation parameter of suspensions or precipitants in a fluid medium sample, said method comprising:
providing at least one micro-cantilever sensor in the fluid medium sample, said micro-cantilever sensor comprising at least two materials having different coefficients of thermal expansion, and having a heater and piezo-resistive sensor integrated therein;
pulsing the heater with one or more electrical pulses to induce heat generation in the micro-cantilever;
sampling the output of the integrated piezo-resistive sensor to characterise a response of the micro-cantilever during sedimentation in the fluid medium sample; and
determining a value of the sedimentation parameter from the characterised response
wherein the method further comprises:
measuring temperature of the fluid medium sample using the micro-cantilever simultaneously with determining the value of the sedimentation parameter; and
correcting the determined value of the sedimentation parameter based on the measured temperature, and
further comprising providing at least two substantially similar micro-cantilevers and wherein the fluid medium sample includes a first fluid medium and a second fluid medium, wherein a first micro-cantilever is placed in the first fluid medium and a second micro-cantilever is placed in the second fluid medium, wherein the method further comprises comparing the output of a piezo-resistive sensor integrated into the first micro-cantilever with the output of a piezo-resistive sensor integrated into the second micro-cantilever when both are immersed in the respective first and second fluid mediums.

14. The method of claim 13, wherein the first fluid medium is a control fluid, the second fluid medium comprises the suspensions, the first micro-cantilever is a control micro-cantilever and the second micro-cantilever is a measurement micro-cantilever.

15. The method of claim 13, wherein the first fluid medium is a first sample of the fluid medium sample comprising the suspensions, the second fluid medium is a second sample of the fluid medium sample comprising the suspensions, the first micro-cantilever is a measurement micro-cantilever in a first position and/or orientation and the second micro-cantilever is a measurement micro-cantilever in a second position and/or orientation.

* * * * *